US010504819B2

(12) United States Patent
Gutala et al.

(10) Patent No.: US 10,504,819 B2
(45) Date of Patent: Dec. 10, 2019

(54) INTEGRATED CIRCUIT PACKAGE WITH ENHANCED COOLING STRUCTURE

(71) Applicant: Altera Corporation, San Jose, CA (US)

(72) Inventors: Ravi Gutala, San Jose, CA (US); Arifur Rahman, San Jose, CA (US); Karthik Chandrasekar, Fremont, CA (US)

(73) Assignee: Altera Corporation, San Jose, CA (US)

( * ) Notice: Subject to any disclaimer, the term of this patent is extended or adjusted under 35 U.S.C. 154(b) by 596 days.

(21) Appl. No.: 14/938,486

(22) Filed: Nov. 11, 2015

(65) Prior Publication Data

US 2017/0133298 A1 May 11, 2017

(51) Int. Cl.
*G01K 7/00* (2006.01)
*H01L 23/473* (2006.01)
*G01K 7/34* (2006.01)
*G01N 25/00* (2006.01)
*H01L 21/48* (2006.01)
*H01L 23/367* (2006.01)
*H01L 23/467* (2006.01)
*H01L 23/498* (2006.01)
*H01L 25/065* (2006.01)
*H01L 23/44* (2006.01)

(52) U.S. Cl.
CPC .......... *H01L 23/473* (2013.01); *G01K 7/343* (2013.01); *G01N 25/00* (2013.01); *H01L 21/486* (2013.01); *H01L 23/3677* (2013.01); *H01L 23/467* (2013.01); *H01L 23/49827* (2013.01); *H01L 25/065* (2013.01); *H01L 21/4882* (2013.01); *H01L 23/367* (2013.01); *H01L 23/44* (2013.01)

(58) Field of Classification Search
CPC combination set(s) only.
See application file for complete search history.

(56) References Cited

U.S. PATENT DOCUMENTS

| 6,351,384 B1 * | 2/2002 | Daikoku ............ F28F 3/02 165/80.3 |
| 7,266,267 B2 | 9/2007 | Bakir et al. |
| 7,532,467 B2 | 5/2009 | Launay et al. |

(Continued)

OTHER PUBLICATIONS

European Patent Office, European Search Report and Opinion for European Patent Application EP 16197872.1, dated Apr. 20, 2017.

(Continued)

*Primary Examiner* — Lisa M Caputo
*Assistant Examiner* — Nasir U. Ahmed

(57) ABSTRACT

An integrated circuit package may include an integrated circuit die having first and second circuit regions and a surface. The first circuit region of the integrated circuit package has an operating temperature that is different than that of the second circuit region. A cooling structure is formed on the surface of the integrated circuit die. The cooling structure includes a group of micropipe interconnects arranged to form a cooling channel that allows for the flow of coolant. The cooling channel includes first and second sub-channels. The first sub-channel has a first size that allows a higher flow rate of the coolant to cool the first circuit region. The second sub-channel has a second size that allows a lower flow rate of the coolant to cool the second circuit region.

20 Claims, 6 Drawing Sheets

(56) References Cited

U.S. PATENT DOCUMENTS

| | | | |
|---|---|---|---|
| 7,545,644 B2 | 6/2009 | Fedorov | |
| 7,832,096 B2* | 11/2010 | Kuczynski | H01L 23/473 |
| | | | 257/714 |
| 7,928,563 B2 | 4/2011 | Bakir et al. | |
| 8,082,978 B2 | 12/2011 | Fedorov | |
| 8,378,453 B2 | 2/2013 | Fedorov et al. | |
| 8,546,930 B2 | 10/2013 | Bakir et al. | |
| 8,563,365 B2 | 10/2013 | King, Jr. et al. | |
| 8,710,625 B2 | 4/2014 | Fedorov et al. | |
| 8,739,856 B2 | 6/2014 | Fedorov et al. | |
| 8,878,340 B1 | 11/2014 | Fedorov et al. | |
| 8,953,314 B1 | 2/2015 | Fedorov | |
| 2005/0139996 A1* | 6/2005 | Myers | H01L 23/473 |
| | | | 257/712 |
| 2006/0103011 A1 | 5/2006 | Andry et al. | |
| 2009/0151923 A1 | 6/2009 | Fedorov | |
| 2009/0284921 A1* | 11/2009 | Colgan | H01L 23/473 |
| | | | 361/699 |
| 2009/0308578 A1* | 12/2009 | Bernstein | H01L 23/473 |
| | | | 165/104.33 |
| 2010/0290188 A1* | 11/2010 | Brunschwiler | H01L 23/473 |
| | | | 361/699 |
| 2011/0205708 A1 | 8/2011 | Andry et al. | |
| 2012/0228779 A1* | 9/2012 | King, Jr. | H01L 23/473 |
| | | | 257/774 |

OTHER PUBLICATIONS

Paragkumar A. Thadesar, et al., "Low-loss Silicon Interposer for Three-dimensional System Integration with Embedded Microfluidic Cooling," 2014 Symposium on VLSI Technology Digest of Technical Papers, 2014, pp. 156-157.

* cited by examiner

INTEGRATED CIRCUIT PACKAGE WITH ENHANCED COOLING STRUCTURE

FIELD OF THE DISCLOSURE

The present disclosure relates to electronic integrated circuit packages, and more particularly, to integrated circuit packages with enhanced cooling structures.

BACKGROUND

In a semiconductor device assembly, an integrated circuit (IC) die (also referred to as a semiconductor chip or "die") may be mounted on a packaging substrate. With increasing need for higher performance and density, many integrated circuit packages have been incorporating more integrated components per unit area. Components may be placed closer or stacked together on printed circuit boards to lower device dimension and cost. For example, die-stacking (e.g., face-to-face die stacking, face-to-back die stacking) integration may be required for three-dimensional (3D) multi-die integrated circuit packages to obtain better performance and higher density.

As logic and power density of the 3D packages increase, device cooling has become a more significant concern. Conventional cooling techniques, which depend on heat sinks on the backs of IC dies to transfer heat into streams of forced air, will not be able to meet the needs of power-hungry devices, especially 3D packages that will pack more processing power into less space. The power generated during high volume operation by such devices may reduce the overall cooling efficiency, and create localized regions of high temperature (i.e., hot spots), which may adversely affect the overall performance and reliability of the devices.

SUMMARY

In accordance with the present invention, apparatuses and methods are provided for creating integrated circuit packages with enhanced cooling structures.

The present invention can be implemented in numerous ways, such as a process, an apparatus, a system, or a device. Several embodiments of the present invention are described below.

An integrated circuit package is disclosed. The integrated circuit package includes an integrated circuit die having first and second circuit regions and a surface. A cooling structure is formed on the surface of the integrated circuit die. The cooling structure includes a group of micropipe interconnects arranged to form a cooling channel that allows for the flow of coolant. The cooling channel includes first and second sub-channels. The first sub-channel has a first size that allows a higher flow rate for cooling the first circuit region using the coolant, and the second sub-channel has a second size that allows a lower flow rate for cooling the second circuit region using the coolant. The integrated circuit package further includes an inlet port connected to the cooling structure for admitting a fluid to pass through the cooling channel in the cooling structure, and an outlet port connected to the cooling structure for expelling the coolant out of the cooling channel in the cooling structure. The inlet port is positioned next to the first circuit region, and the outlet port is positioned next to the second circuit region.

A method of fabricating a cooling system for an integrated circuit package is disclosed. The method includes forming a first fluidic channel of a first size in a first region of the integrated circuit package at a back surface of an integrated circuit, and forming a second fluidic channel of a second size different than the first size in a second region of the integrated circuit package at the back surface of the integrated circuit. The first fluidic channel is between first micropipe interconnects that are spaced apart by at least a first distance, and the second fluidic channel is between second micropipe interconnects that are spaced apart by at least a second distance. The first and second micropipe interconnects are coupled to the integrated circuit. The method further includes forming a first circuit region having a first heat density in the integrated circuit next to the first fluidic channel, and forming a second circuit region having a second heat density that is different than the first heat density in the integrated circuit next to the second fluidic channel.

A method for testing a cooling structure in an integrated circuit housing is disclosed. The method includes providing a coolant to the cooling structure in the integrated circuit housing. The cooling structure includes micropipe interconnects and a cooling channel between the micropipe interconnects, where the cooling channel is next to a surface of an integrated circuit die. The method further includes determining if the coolant is cooling the integrated circuit die by measuring temperatures in the integrated circuit die using temperature sensors that are located in the integrated circuit die. To do so, capacitances of through-silicon-vias in the integrated circuit die that are coupled to the micropipe interconnects are measured using the temperature sensors.

Further features of the invention, its nature and various advantages, will be more apparent from the accompanying drawings and the following detailed description of the preferred embodiments.

DETAILED DESCRIPTION

The embodiments provided herein include integrated circuit structures and packaging techniques for creating an integrated circuit packages with enhanced cooling structure.

Figure 1:
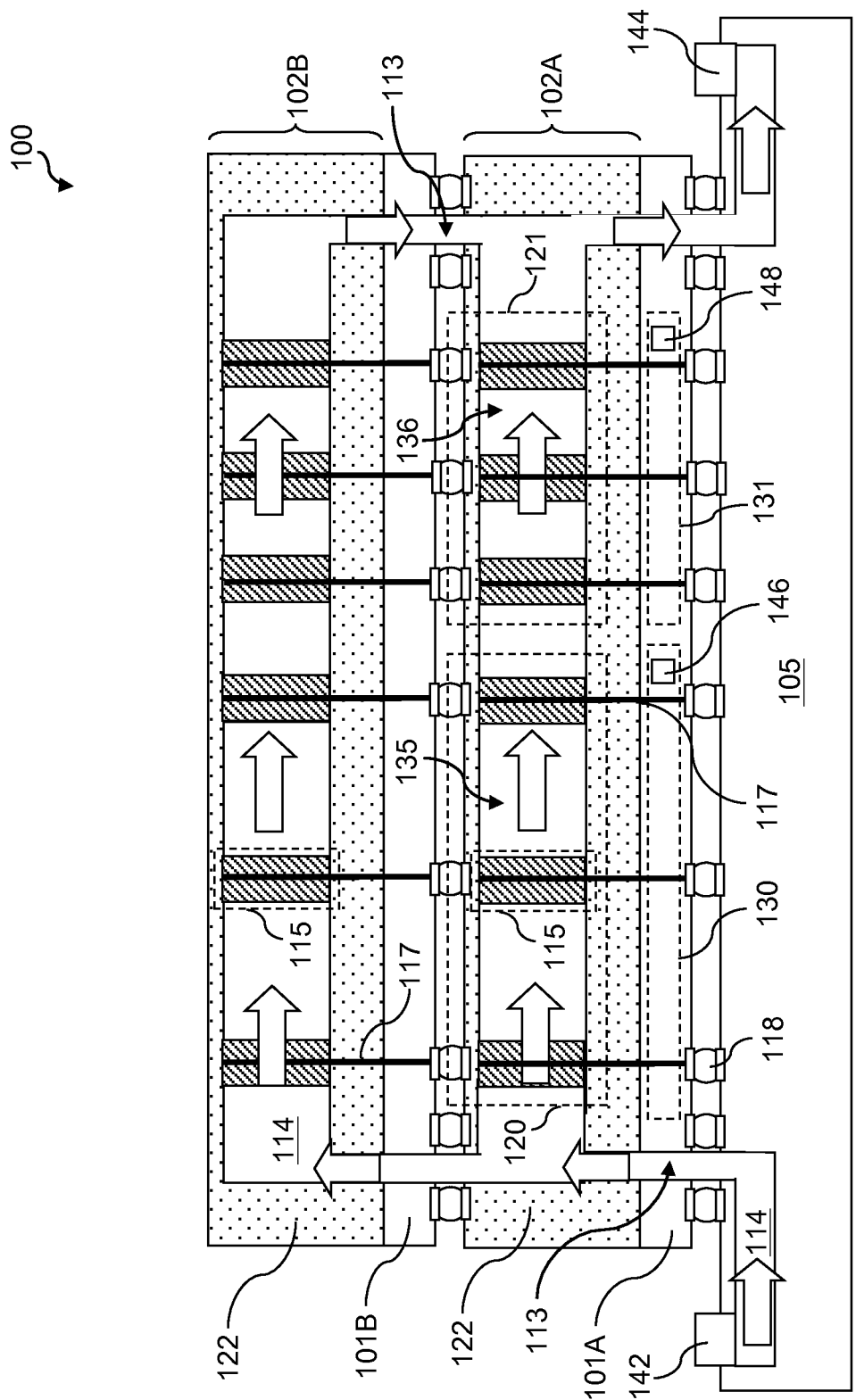
FIG. 1 shows a cross section view of an illustrative three-dimensional (3D) integrated circuit package having a microfluidic cooling structure in accordance with one embodiment of the present invention.

FIG. 1 shows a cross section view of an illustrative three-dimensional (3D) integrated circuit (IC) package 100 with micropipe interconnects and heat sinks in accordance with one embodiment of the present invention. 3D IC package 100 includes IC die 101B stacked on IC die 101A. IC dies 101A and 101B may be field-programmable gate array (FPGA) dies or other types of IC dies, such as processor IC dies, memory IC dies, analog IC dies, or any combination thereof. In one embodiment, IC dies 101A and 101B are homogeneous dies. In another embodiment, IC dies 101A and 101B are heterogeneous dies. As shown in FIG. 1, IC die 101A may be disposed over package substrate 105 (e.g., IC die 101A may be mounted on package substrate 105) through solder bumps 118. It should be appreciated that even though two IC dies (e.g., IC dies 101A and 101B) are shown in the embodiment of FIG. 1, depending on the required functionality of the integrated circuit package, two or more IC dies may be included within a 3D integrated circuit package such as 3D package 100.

During the operation of 3D IC package 100, heat generated by IC dies 101A and 101B may create localized regions of high temperature (i.e., hot spots) within the package, which may result in power losses as well as damage to heat sensitive components. To enable management of heat produced during the operation of 3D IC package 100, a microfluidic cooling structure (e.g., cooling structures 102A and 102B) may be implemented within 3D IC package 100.

As shown in FIG. 1, each cooling structure 102A and 102B includes a monolithically integrated microchannel heat sink 122; electrical through-silicon vias (e.g., filled with copper) (e.g., TSEV 117); fluidic through-silicon (hollow) vias (e.g., TSFVs 113) for fluidic routing in the 3D stack; and solder bumps (electrical I/Os) (e.g., solder bumps 118) and microscale polymer pipes (fluidic I/Os) (e.g., micropipe interconnects 115) on the side of the IC die opposite to microchannel heat sink 122. Microscale fluidic interconnection between IC dies 101A and 101B is enabled by the TSFVs 113 and micropipe interconnects 115. IC dies 101A and 101B may be designed such that when they are stacked, each IC die makes electrical and fluidic interconnection to the other IC die. As a result, power delivery and signaling can be supported by the electrical interconnects (solder bumps 118 and TSEVs 117), and heat removal for each IC die can be supported by the fluidic I/Os and microchannel heat sinks 122.

In addition, a liquid coolant (e.g., coolant 114) is delivered to cooling structures 102A and 102B within the 3D stack using a thermofluidic interconnect network (or cooling network) that is composed of micropipe interconnects 115 and TSFVs 113. Such a coolant can be many materials capable of absorbing heat from 3D IC package 100, such that heat is moved from 3D IC package 100. For example, the liquid coolant may be distilled water or a mixture of water and anti-freezing solution, such as, propylene glycol or the like. Accordingly, the cooling network may include one or more micro fluidic channels (or fluidic channels) that allows for the flow of coolant 114. A fluidic channel is typically formed by an arrangement of at least two or more micropipe interconnects 115. The cooling network in 3D IC package 100 may include horizontal, diagonal, vertical, or a combination thereof, fluidic channels (or coolant channels) to route coolant through 3D IC package 100. In some embodiments, the fluidic channels can be implemented on all IC dies within a homogeneous die stack. In some other embodiments, a fluidic channel can only be implemented on the IC die with higher heat dissipation within a heterogeneous die stack.

In one embodiment, non-uniform heat removal regions can be created in each cooling structure by modifying one or more dimensions of the fluidic channels. To do so, the size (e.g., diameter) of micropipe interconnects 115 can be adjusted so that different sized fluidic channels can be formed in each heat removal region.

As cooling structures 102A and 102B are substantially similar to each other, only cooling structure 102A will be explained as an example in greater detail. For example, as shown in FIG. 1, cooling structure 102A includes heat removal region 120 having a first sub-fluidic channel (e.g., fluidic channel 135) between a first subset of micropipe interconnects 115, and heat removal region 121 having a second sub-fluidic channel (e.g., fluidic channel 136) between a second subset of micropipe interconnects 115. The fluidic channels are the spaces between the micropipe interconnects that allow the flow of coolant. In an exemplary embodiment, the size of fluidic channel 135 may be larger than the size of fluidic channel 136, which gives a higher flow rate to allow a larger volume of coolant to flow through fluidic channel 135 of 3D IC package 100. For example, the volume of fluidic channel 135 may be larger than the volume of fluidic channel 136. Hence, heat removal region 120 may provide a higher heat removal rate than that of heat removal region 121.

In addition, different amounts of coolant that flow through cooling structure 102A may affect the capacitance of micropipe interconnects 115. For example, the capacitance in a particular area of the IC package can be adjusted by way of increasing or decreasing the size (e.g., volume) of the sub fluidic channels between micropipe interconnects 115. To ensure optimal cooling within 3D IC package 100 among circuit regions of different heat densities in IC die 101A, the circuit regions having different heat densities in IC die 101A can be disposed next to different heat removal regions in cooling structure 102A.

Based on the exemplary embodiment described above, circuit regions with higher heat densities can be formed next to heat removal regions having larger-sized fluidic channels, and circuit regions with lower heat densities can be formed next to heat removal regions having smaller-sized fluidic channels. For example, circuit region 130 in IC die 101A that includes circuit elements of higher heat output (e.g., a processor circuit) may be formed next to heat removal region 120, and circuit region 131 in IC die 101A that includes circuit elements of lower heat output (e.g., a logic array circuit) may be formed next to the heat removal region 121. Such a configuration provides an optimum heat transfer and better temperature uniformity across the IC dies in 3D IC package 100. In the case of programmable integrated circuit dies, placement of circuit elements having different heat outputs can be configured (or reconfigured) on the fly, e.g., using a computer-aided design (CAD) tool (not shown), based on the location of the fluidic channels (or heat removal regions) in the cooling structures to increase cooling efficiency.

As further shown in FIG. 1, coolant 114 can be routed through package substrate 105 of 3D IC package 100. Package substrate 105 may include inlet port 142 and outlet port 144 for transporting coolant 114 through 3D IC package 100. The coolant 114 typically increases in temperature as it flows through 3D IC package 100 from inlet port 142 to outlet port 144. Therefore, to increase heat removal efficiency of the coolant, inlet port 142 may be positioned next to circuit region 130 of IC die 101A, and outlet port 144 is positioned next to circuit region 131 of IC die 101A. Both inlet port 142 and outlet port 144 are positioned in such a manner that when the coolant flows (indicated by arrows) through 3D IC package 100, high-temperature, higher heat output circuit region 130 is cooled first by the coolant 114 while the coolant it cooler, followed by low-temperature, lower heat output circuit region 131 being cooled by the coolant 114.

After manufacturing, the cooling structures can be tested to determine whether the coolant is cooling 3D IC package 100. For example, cooling structure 102A can be tested by measuring temperatures on circuit regions 130 and 131 of IC die 101A using temperature sensors (e.g., temperature sensors 146 and 148, respectively) that are located in IC die 101A. If the measured temperature of each circuit region meets a predetermined cooling temperature, this indicates that cooling structure 102A is working as expected across IC die 101A.

Figure 2A:
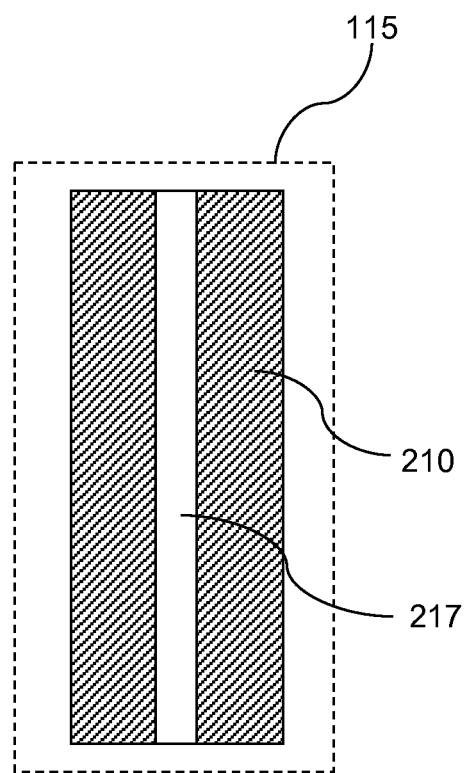
FIGS. 2A-2B show cross section views of an illustrative micropipe interconnect in accordance with one embodiment of the present invention.
Figure 2B:
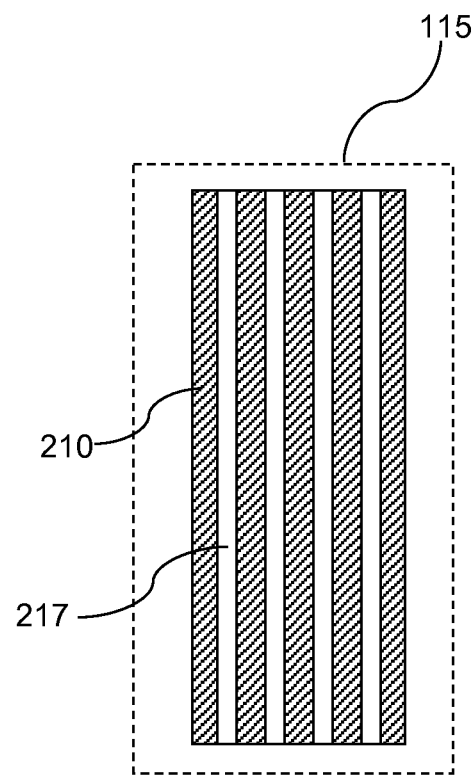

FIGS. 2A-2B show cross section views of an illustrative micropipe interconnect 115 of FIG. 1 in accordance with one embodiment of the present invention. Micropipe interconnect 115 includes silicon micropin-fin 210 having one (FIG. 2A) or more through-silicon-vias (TSVs) 217 (FIG. 2B), which may extend between the top surface and the bottom surface of micropin-fin 210 to form signal transmission structures. In one embodiment, micropipe interconnects 115 may electrically couple to TSEVs 117 of FIG. 1 to provide electrical communication between IC die 101A and IC die 101B within 3D IC package 100. In an embodiment, TSV 217 of FIG. 2A is an example of part of one or more of TSEVs 117 shown in FIG. 1.

In one embodiment, cooling structure 102A can be tested (e.g., using temperature sensors 146 and 148 of FIG. 1) by measuring capacitances of TSVs 217 in micropipe interconnects 115 to determine if a coolant (e.g., coolant 114 of FIG. 1) is flowing through cooling structure 102A. Each TSV 217 has a predetermined capacitance value, which may change in response to the dielectric constant of the coolant in the adjacent fluidic channel changing. Generally, a water-based coolant (dielectric constant=80) has a higher dielectric constant than air (dielectric constant=1). When the coolant flows through the fluidic channels between micropipe interconnects 115 in cooling structure 102A, the capacitances of TSVs 217 in micropipe interconnects 115 may increase. In the case when air is present in the coolant flow path (i.e., no coolant flow), the capacitance in TSVs 217 remains unchanged.

Figure 3:
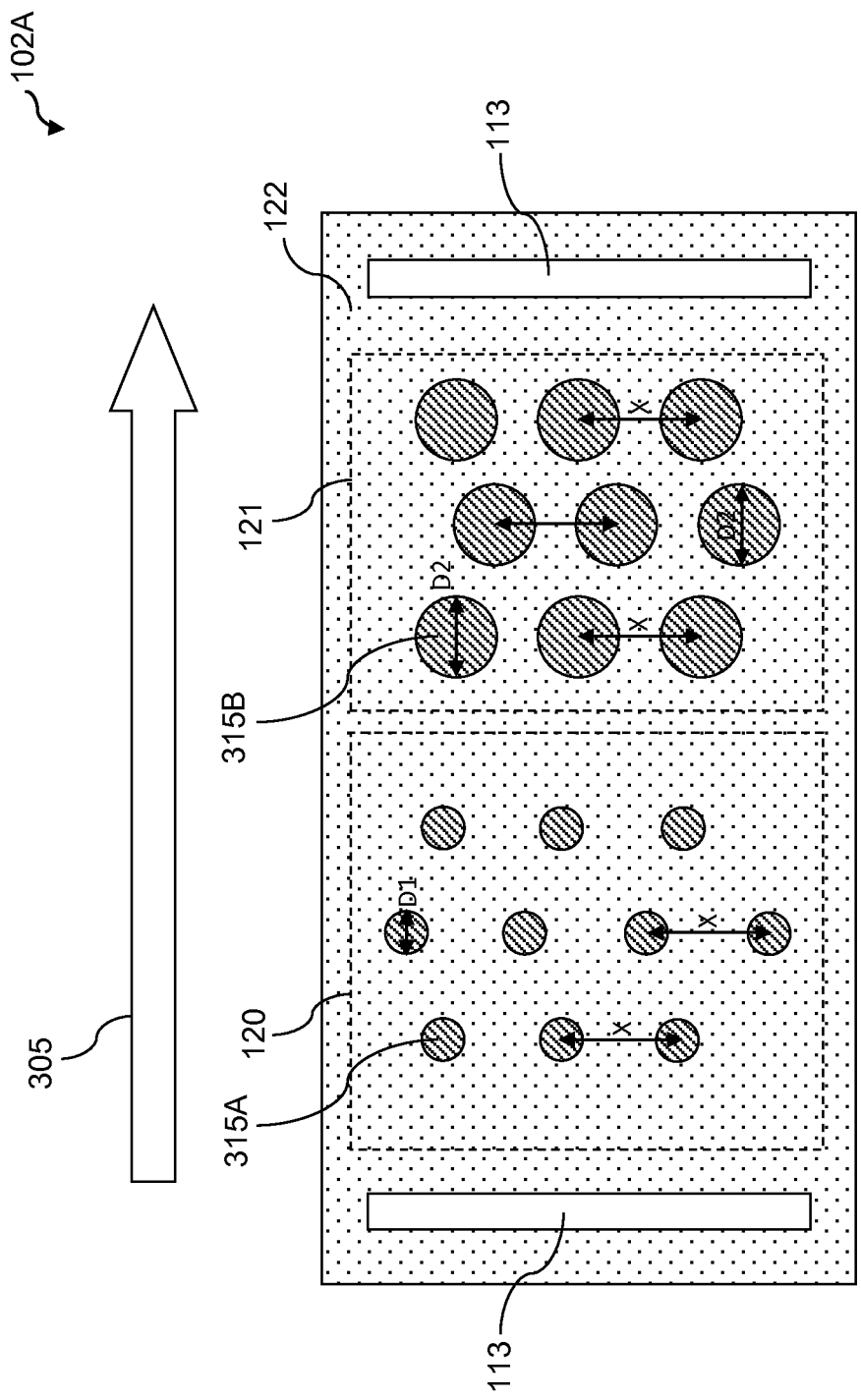
FIG. 3 shows a top view of an illustrative cooling structure of an integrated circuit package in accordance with one embodiment of the present invention.
Figure 4:
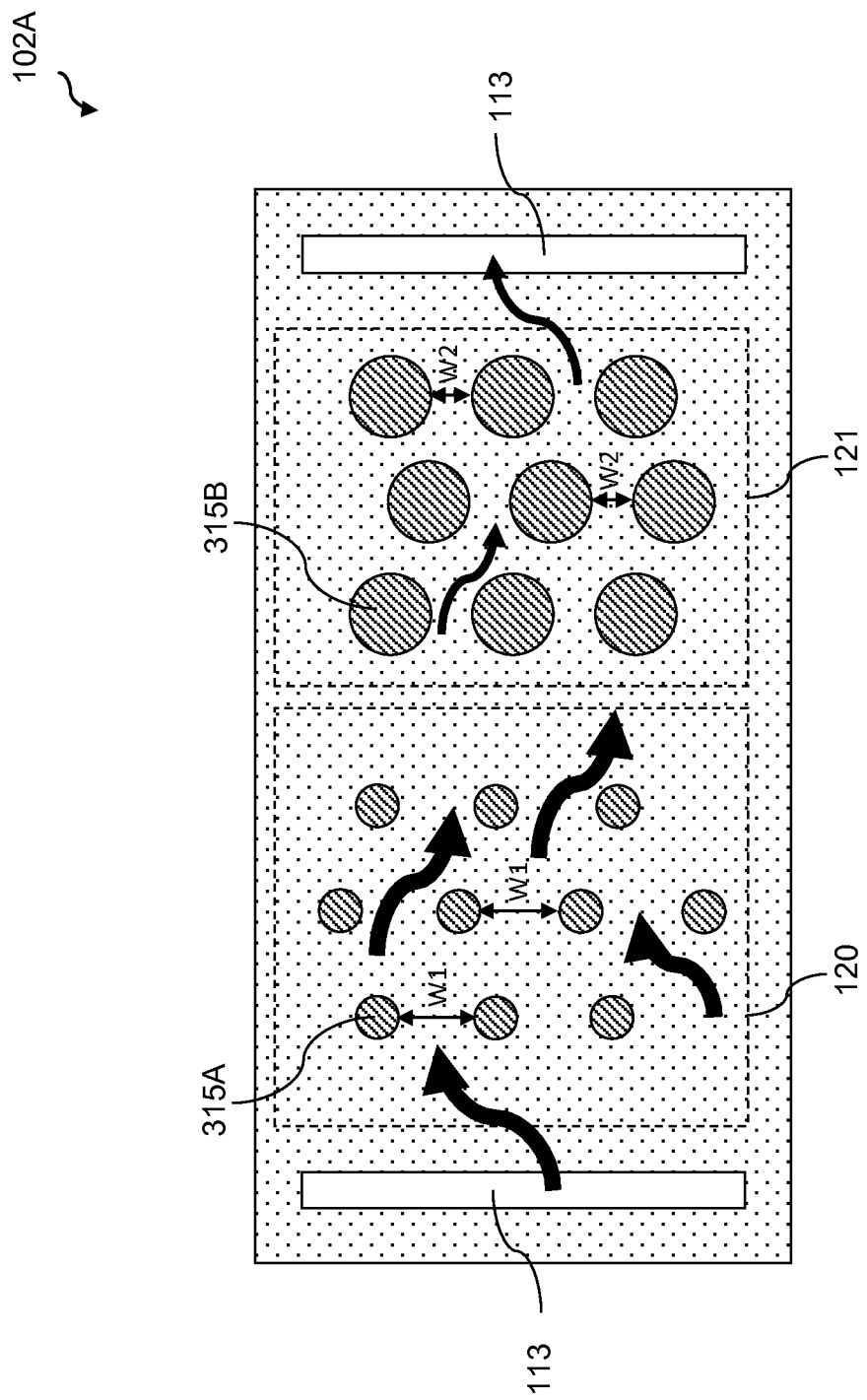
FIG. 4 shows a top view illustrating fluid flow through a cooling structure in accordance with embodiments of the present invention.

FIGS. 3 and 4 show top views of an illustrative cooling structure 102A with micropipe interconnects 315A and 315B having varied sizes (e.g., diameters) that are formed on a surface of an integrated circuit die (e.g., IC dies 101A and 101B) in accordance with one embodiment of the present invention. Micropipe interconnects 315A and 315B may be part of micropipe interconnects 115 of FIG. 1. It should be appreciated that for the sake of brevity, components already shown in cooling structure 102A of FIG. 1 (e.g., microchannel heat sinks 122, and through-silicon fluidic vias (TSFV) 113) and described above will not be repeated.

As described above, cooling structure 102A may include one or more fluidic channels configured to facilitate the flow of a fluid (e.g., coolant 114 of FIG. 1) for cooling 3D IC package 100 of FIG. 1. A fluidic channel is typically formed by an arrangement of two or more micropipe interconnects. As shown in FIG. 3, micropipe interconnects 315A and 315B may be separated by gaps, which may define the fluidic channels therebetween. The distance between adjacent micropipe interconnects may be referred to as pitch or interconnect pitch. For instance, micropipe interconnects 315A may be spaced apart from each other by a distance X. Similarly, micropipe interconnects 315B may also be spaced apart from each other by the same distance X. The distance of the interconnect pitch may be measured from the center of one micropipe interconnect to the center of an adjacent micropipe interconnect. Distance X may be, for example about 200 micrometers (μm).

In one embodiment, one or more heat removal regions may be formed on cooling structure 102A for cooling different circuit regions in the 3D IC package 100. Each heat removal region may include a subset of micropipe interconnects each having a size (e.g., diameter) that form at least one fluidic channel, which allows the flow of coolant to cool a corresponding circuit region in an IC die. For example, as shown in FIG. 3, two heat removal regions (e.g., regions 120 and 121) are formed to cool the respective circuit regions 130 and 131. Region 120 includes a first subset of micropipe interconnects (e.g., micropipe interconnects 315A), each having a diameter D1. The diameter D1 of each micropipe interconnect 315A may be, for example, about 50 micrometers (μm). Accordingly, region 121 includes a second subset of micropipe interconnects (e.g., micropipe interconnects 315B), each having a diameter D2. The diameter D2 of each micropipe interconnect 315B may be, for example, about 150 μm.

In one embodiment, different sized micropipe interconnects may form fluidic channels of different dimensions. The term "dimension" refers to the distance between adjacent micropipe interconnects measured from the side edge of one micropipe interconnect to the side edge of an adjacent micropipe interconnect. For instance, as illustrated in FIG. 4, micropipe interconnects 315A in region 120 may form a first set of fluidic channels, each having a dimension W1. The dimension W1 of the first fluidic channels in region 120 may be, for example, about 150 μm. Accordingly, micropipe interconnects 315B in region 121 may form a second set of fluidic channels, each having a dimension W2. The dimension W2 of the second fluidic channels in region 121 may be, for example, about 50 μm.

As shown in FIG. 3, the flow direction of the coolant is indicated by arrow 305 within cooling structure 102A. In one embodiment, the larger size fluidic channels formed between micropipe interconnects 315A may permit the flow of coolant at a higher volume to cool circuit region 130 of FIG. 1, which has a higher heat density than that of circuit region 131 of FIG. 1. Accordingly, the smaller size fluidic channels formed between micropipe interconnects 315B may permit the flow of coolant at a lower volume to cool circuit region 131, which has a lower heat density than that of circuit region 130. Such a configuration may provide uniform temperature control across the circuit regions and subsequently improve reliability of the 3D IC package.

Figure 5:
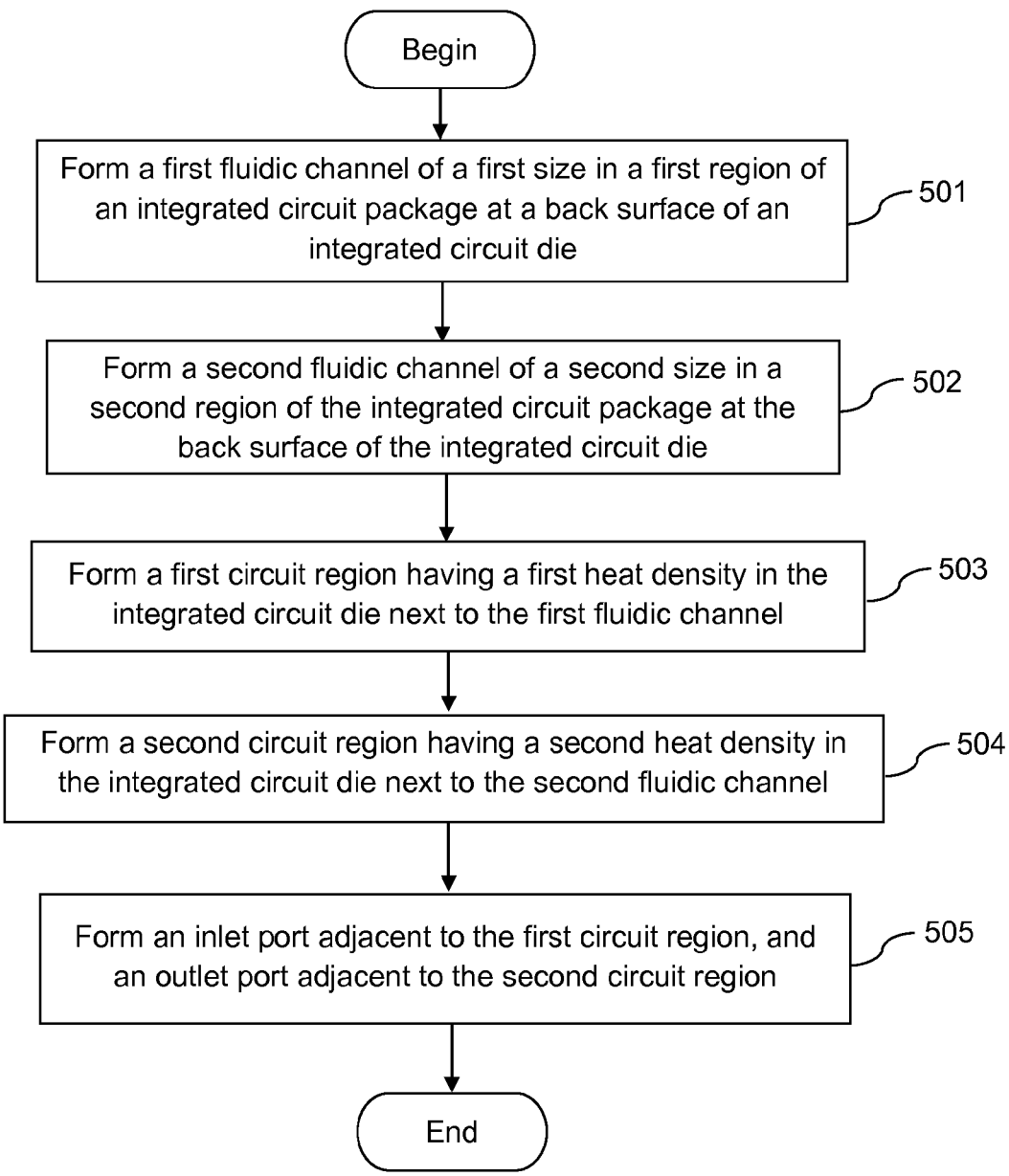
FIG. 5 is a flow chart of illustrative steps to fabricate a cooling structure in an integrated circuit package in accordance with one embodiment of the present invention.

FIG. 5 is a flow chart of illustrative steps to fabricate a cooling structure in an integrated circuit (IC) package in accordance with one embodiment of the present invention. It should be appreciated that the embodiments of FIGS. 1, 2A-2B, 3 and 4 may be used as examples to implement the steps described below. In one embodiment, the IC package may be a three-dimensional (3D) IC package.

The cooling structure (e.g., cooling structures 102A and 102B of FIG. 1) may be composed of micropipe interconnects (e.g., micropipe interconnects 115 of FIG. 1) and through-silicon fluidic (hollow) vias (TSFV) (e.g., TSFVs 113 of FIG. 1), which may collectively form a thermofluidic interconnect network (i.e., cooling network) in the cooling structure. The thermofluidic interconnect network may include one or more fluidic channels having different dimensions (i.e., different sizes), which may allow the flow of a fluid coolant (e.g., coolant 114 of FIG. 1) that absorbs heat from IC dies in the IC package. This heat exchange system allows the coolant to control and/or manage heat dissipated by the IC package.

At step 501, a first fluidic channel of a first size is formed in a first region of the IC package at a back surface of an IC die. As shown in FIGS. 1 and 3, the first fluidic channel is formed via an arrangement of a first subset of micropipe interconnects (e.g., micropipe interconnects 315A) in heat removal region 120 to facilitate heat removal for a corresponding circuit region (e.g., circuit region 130) in IC die 101A of 3D IC package 100. Adjacent micropipe interconnects 315A may form a group of sub-fluidic channels with larger dimensions, due to the smaller sizes of interconnects 315A. A larger fluidic channel allows a larger volume of coolant to flow through, which may cool a high-temperature circuit region.

At step 502, a second fluidic channel of a second size is formed in a second region of the IC package at the back surface of the IC die. The first and second sizes of the first and second fluidic channels may be, for example, two different dimensions and/or two different volumes of the first and second fluidic channels. As shown in FIGS. 1 and 3, the second fluidic channel is formed via an arrangement of a second subset of micropipe interconnects (e.g., micropipe interconnects 315B) in heat removal region 121 to facilitate heat removal for a corresponding circuit region (e.g., circuit region 131) in IC die 101A of 3D IC package 100. Adjacent micropipe interconnects 315B may form a group of sub-fluidic channels with smaller dimensions, due to the larger sizes of interconnects 315B. The first fluidic channel may allow a larger volume of coolant to flow through it than the second fluidic channel.

At step 503, a first circuit region having a first heat density in the integrated circuit die is formed next to the first fluidic channel. For example, as shown in FIG. 1, circuit region 130 may be formed next to heat removal region 120 where the first fluidic channel is formed. Circuit region 130 may include circuit elements that generate a higher heat output, such as a processor circuit, than the circuit elements in region 131. In one embodiment, the larger fluidic channel in region 120 may allow a higher volume of coolant to flow through, which may cool a high-temperature circuit region such as circuit region 130.

At step 504, a second circuit region having a second heat density in the integrated circuit die is formed next to the second fluidic channel. For example, as shown in FIG. 1, circuit region 131 may be formed next to heat removal region 121 where the second fluidic channel is formed. Circuit region 131 may include circuit elements that generate lower heat output, such as a logic array circuit or programmable logic circuits, than the circuit elements in region 130. In one embodiment, the smaller fluidic channel in region 121 may allow a lower volume of coolant to flow through, which may cool a low-temperature circuit region such as circuit region 131.

At step 505, an inlet port is formed next to the first circuit region, and an outlet port is formed next to the second circuit region. As shown in FIG. 1, inlet port 142 and outlet port 144 are formed in package substrate 105 for transporting coolant through 3D IC package 100. Inlet port 142 may admit the coolant to pass through the first and second fluidic channels within cooling structure 102A. Accordingly, outlet port 144 may expel the coolant to pass out of the first and second fluidic channels within cooling structure 102A. In one embodiment, inlet port 142 may be positioned next to circuit region 130 of IC die 101, and outlet port 144 is positioned next to circuit region 131 of IC die 101. Such arrangement allows circuit region 130 to be cooled first, followed by circuit region 131 when the coolant flows through cooling structure 102A in package 100, resulting in an improved heat removal efficiency at multiple circuit regions in the IC package.

The present exemplary embodiments may be practiced without some or all of these specific details described with reference to the respective embodiments. In other instances, well-known operations have not been described in detail in order not to obscure unnecessarily the present embodiments.

The methods and apparatuses described herein may be incorporated into any suitable circuit. For example, the methods and apparatuses may be incorporated into numerous types of devices such as microprocessors or other integrated circuits. Exemplary integrated circuits include programmable array logic (PAL), programmable logic arrays (PLAs), field programmable logic arrays (FPGAs), electrically programmable logic devices (EPLDs), electrically erasable programmable logic devices (EEPLDs), logic cell arrays (LCAs), field programmable gate arrays (FPGAs), application specific standard products (ASSPs), application specific integrated circuits (ASICs), and microprocessors, just to name a few.

Although the method operations were described in a specific order, it should be understood that other operations may be performed in between described operations, described operations may be adjusted so that they occur at slightly different times or described operations may be distributed in a system which allows the occurrence of the processing operations at various intervals associated with the processing, as long as the processing of the overlay operations are performed in a desired way.

What is claimed is:
1. An integrated circuit package comprising:
    a single integrated circuit die comprising first and second circuit regions and a surface;
    a cooling structure on the surface of the integrated circuit die, wherein the cooling structure comprises a plurality of micropipe interconnects arranged to form a cooling channel that allows for the flow of coolant, and wherein the cooling channel comprises:
        a first sub-channel having a first size between a first subset of the micropipe interconnects for cooling the first circuit region using the coolant; and
        a second sub-channel having a second size between a second subset of the micropipe interconnects for cooling the second circuit region using the coolant, wherein the second size is different than the first size;
    an inlet port connected to the cooling structure for admitting the coolant to pass through the first and second sub-channels in the cooling channel of the cooling structure, wherein the inlet port is positioned next to the first circuit region; and
    an outlet port connected to the cooling structure for expelling the coolant out of the first and second sub-channels in the cooling channel of the cooling structure, wherein the outlet port is positioned next to the second circuit region,
    wherein the first circuit region of the integrated circuit die generates a higher heat density than the second circuit region of the integrated circuit die when the integrated circuit die is operating, wherein the micropipe interconnects in the first subset each have a first diameter, and wherein the micropipe interconnects in the second subset each have a second diameter that is different than the first diameter such that the first subset of the micropipe interconnects permit the flow of coolant at a higher volume to cool the first circuit region than the flow of coolant permitted by the second subset of the micropipe interconnects to the second circuit region.
2. The integrated circuit package defined in claim 1, wherein the first size of the first sub-channel is larger than the second size of the second sub-channel.

3. The integrated circuit package defined in claim 2, wherein the cooling structure comprises a monolithically integrated heat sink.

4. The integrated circuit package defined in claim 3, wherein the first circuit region comprises a processor circuit.

5. The integrated circuit package defined in claim 4, wherein the second circuit region comprises a logic array circuit.

6. The integrated circuit package defined in claim 3, wherein the cooling structure further comprises:
a substrate adapted to allow the flow of the coolant through the first and second sub-channels in the cooling channel.

7. The integrated circuit package defined in claim 6, wherein the coolant comprises water.

8. The integrated circuit package defined in claim 2, wherein the first circuit region has an uncooled operating temperature that is higher than that of the second circuit region.

9. The integrated circuit package defined in claim 8, further comprising:
an additional integrated circuit die.

10. The integrated circuit package defined in claim 9, wherein the coolant is selected from a group consisting of gas and liquid.

11. The integrated circuit package defined in claim 1, wherein each of the micropipe interconnects comprises conductors that connect to through-silicon-vias in the integrated circuit die.

12. The integrated circuit package defined in claim 1, wherein each of the micropipe interconnects in each of the first and second subsets comprises a micropin-fin that comprises at least two vias that extend between a top surface and a bottom surface of the micropin-fin and that connect to the integrated circuit die.

13. The integrated circuit package defined in claim 1, wherein the integrated circuit die comprises a field programmable gate array.

14. An integrated circuit package comprising:
a single integrated circuit die comprising first and second circuit regions; and
a cooling structure on a surface of the integrated circuit die, wherein the cooling structure comprises micropipe interconnects arranged to form a cooling channel that allows for the flow of coolant, and wherein the cooling channel comprises:
a first sub-channel between a first subset of the micropipe interconnects for cooling the first circuit region using the coolant; and
a second sub-channel between a second subset of the micropipe interconnects for cooling the second circuit region using the coolant;
an inlet port connected to the cooling structure for admitting the coolant to pass through the first and second sub-channels in the cooling channel of the cooling structure, wherein the inlet port is positioned next to the first circuit region; and
an outlet port connected to the cooling structure for expelling the coolant out of the first and second sub-channels in the cooling channel of the cooling structure, wherein the outlet port is positioned next to the second circuit region,
wherein the first circuit region of the integrated circuit die generates a higher heat density than the second circuit region of the integrated circuit die when the integrated circuit die is operating, wherein the micropipe interconnects in the first subset each have a first diameter, and wherein the micropipe interconnects in the second subset each have a second diameter that is different than the first diameter such that the first subset of the micropipe interconnects permit the flow of coolant at a higher volume to cool the first circuit region than the flow of coolant permitted by the second subset of the micropipe interconnects to the second circuit region.

15. The integrated circuit package defined in claim 14, wherein the cooling structure comprises a monolithically integrated heat sink.

16. The integrated circuit package defined in claim 14, wherein the first circuit region has an uncooled operating temperature that is higher than that of the second circuit region.

17. The integrated circuit package defined in claim 14, wherein the cooling structure further comprises:
a substrate adapted to allow the flow of the coolant through the first and second sub-channels in the cooling channel.

18. The integrated circuit package defined in claim 14, wherein each of the micropipe interconnects comprises multiple conductors that connect to through-silicon-vias in the integrated circuit die.

19. The integrated circuit package defined in claim 14, wherein each of the micropipe interconnects in each of the first and second subsets comprises a micropin-fin that comprises at least two vias that extend between a top surface and a bottom surface of the micropin-fin and that connect to the integrated circuit die.

20. The integrated circuit package defined in claim 14, wherein the integrated circuit die comprises a field programmable gate array.

* * * * *